United States Patent
Kamiyama et al.

(10) Patent No.: US 6,932,788 B2
(45) Date of Patent: Aug. 23, 2005

(54) SUCTION DEVICE WITH IRRIGATION

(75) Inventors: Hiroyasu Kamiyama, Asahikawa (JP); Nobuhiro Kagaminuma, Kohriyama (JP); Hidetoshi Kashiwazaki, Sapporo (JP)

(73) Assignee: Johnson & Johnson Kabushiki Kaisha, Tokyo (JP)

( * ) Notice: Subject to any disclaimer, the term of this patent is extended or adjusted under 35 U.S.C. 154(b) by 452 days.

(21) Appl. No.: 09/798,709

(22) Filed: Mar. 2, 2001

(65) Prior Publication Data

US 2001/0037082 A1 Nov. 1, 2001

(30) Foreign Application Priority Data

Mar. 3, 2000 (JP) ........................................ 2000-059388

(51) Int. Cl.[7] ......................... A61M 3/00; A61M 25/16; A61M 25/18
(52) U.S. Cl. ......................................... 604/43; 604/534
(58) Field of Search .......................... 604/27, 131, 30, 604/32, 35, 39, 40, 43, 119, 284, 534; 606/107

(56) References Cited

U.S. PATENT DOCUMENTS

| | | | | |
|---|---|---|---|---|
| 4,560,373 A | * | 12/1985 | Sugino et al. | 601/169 |
| 4,836,199 A | * | 6/1989 | Palmer | 128/207.16 |
| 5,224,929 A | * | 7/1993 | Remiszewski | 137/596.2 |
| 5,374,244 A | * | 12/1994 | Clement et al. | 604/164.11 |
| 5,514,089 A | * | 5/1996 | Walbrink et al. | 604/119 |
| 5,902,264 A | * | 5/1999 | Toso et al. | 600/130 |
| 6,086,554 A | * | 7/2000 | Humphreys et al. | 285/921 |
| 6,179,807 B1 | * | 1/2001 | Henniges et al. | 604/35 |
| 6,364,853 B1 | * | 4/2002 | French et al. | 137/596.2 |

FOREIGN PATENT DOCUMENTS

| JP | 62109/1988 | 4/1988 |
|---|---|---|
| JP | 86560/1990 | 7/1990 |

* cited by examiner

Primary Examiner—Manuel Mendez
Assistant Examiner—Mark K. Han

(57) ABSTRACT

A suction device with an irrigation function exhibits reduced occurrence of jamming and can be easily manipulated. A flexible tube 21 is removably connected to a flexible tube connection 22 of a suction device body 20. A suction path 25 is substantially straightly aligned with the flexible tube connection 22. An irrigation path 27 is formed as a branch path of the suction path 25. When a rotation lever 31 is not pressed, the suction path 25 communicates with the flexible tube 21. As the lever 31 is pressed, the communication is disconnected and the irrigation path 27 begins to communicate with the flexible tube 21 through a zero point state.

11 Claims, 15 Drawing Sheets

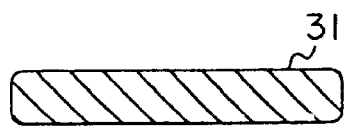
FIG. 5a
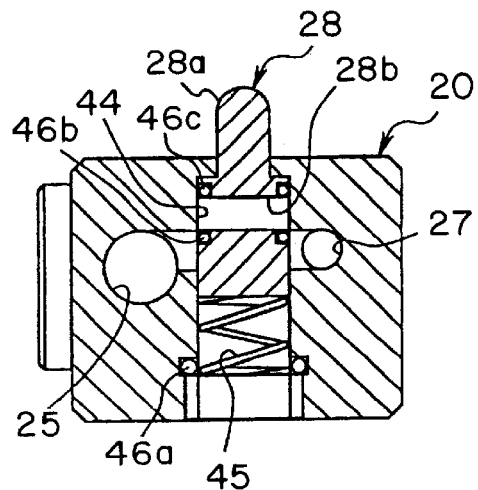
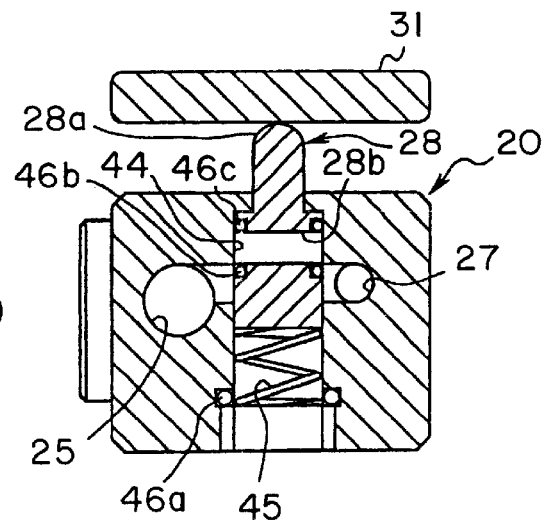
FIG. 5b
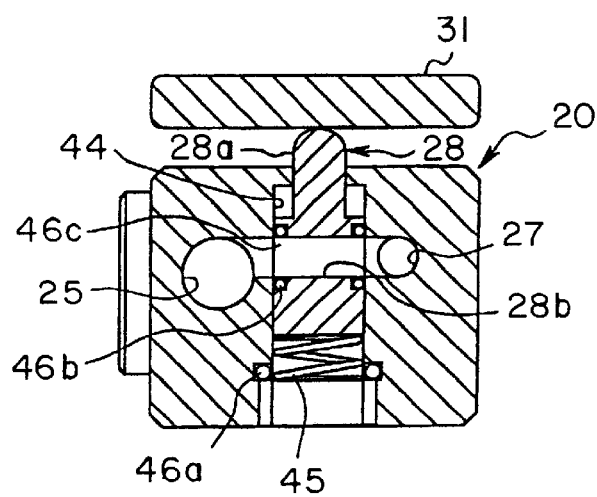
FIG. 5c

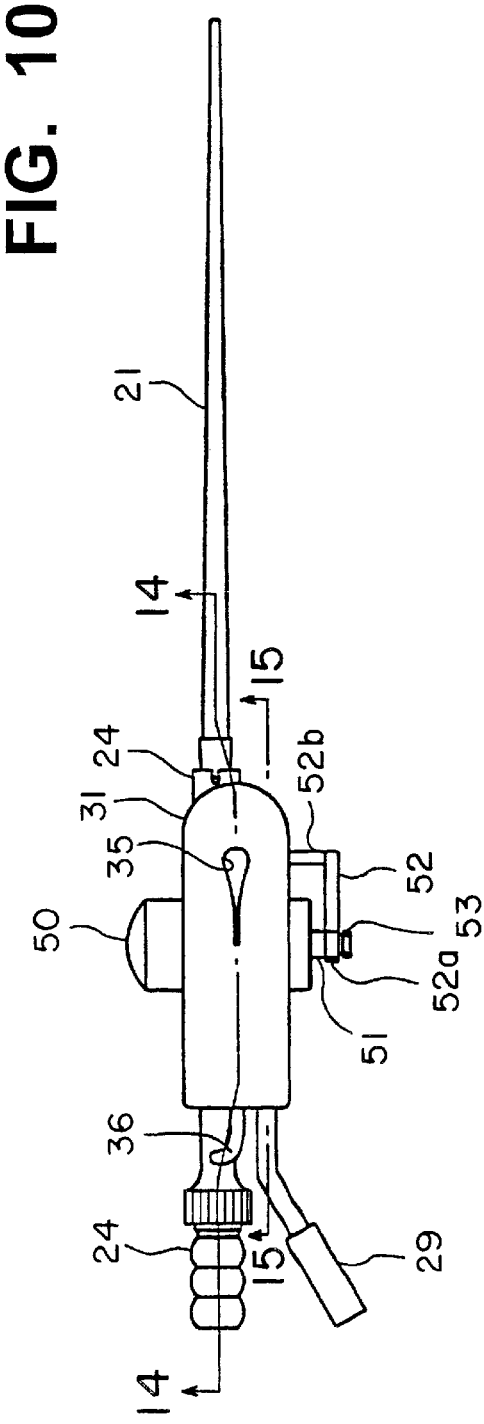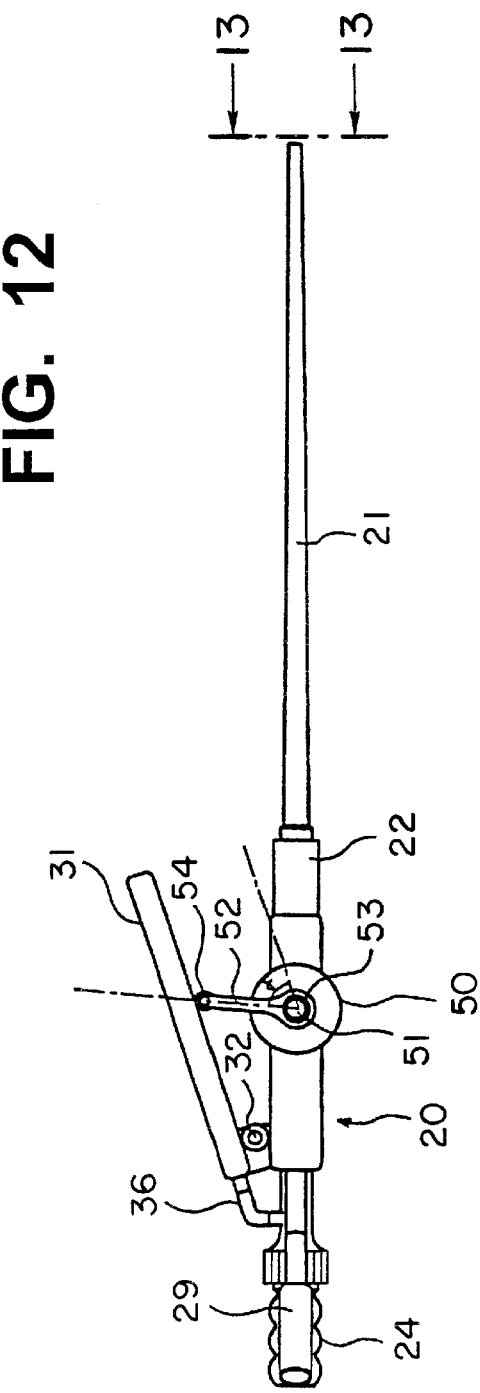

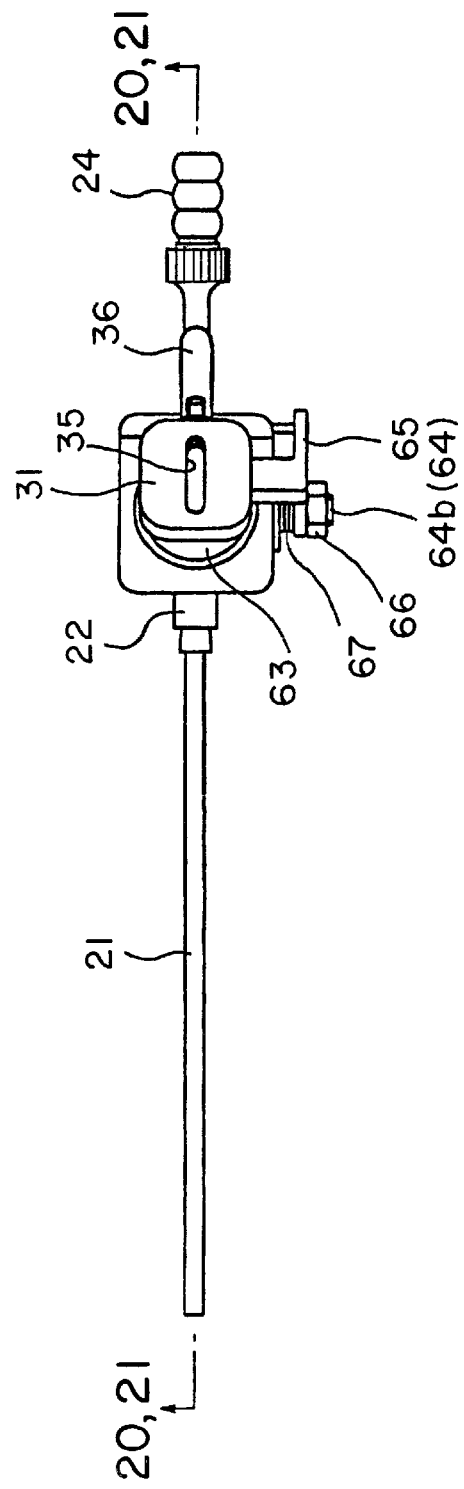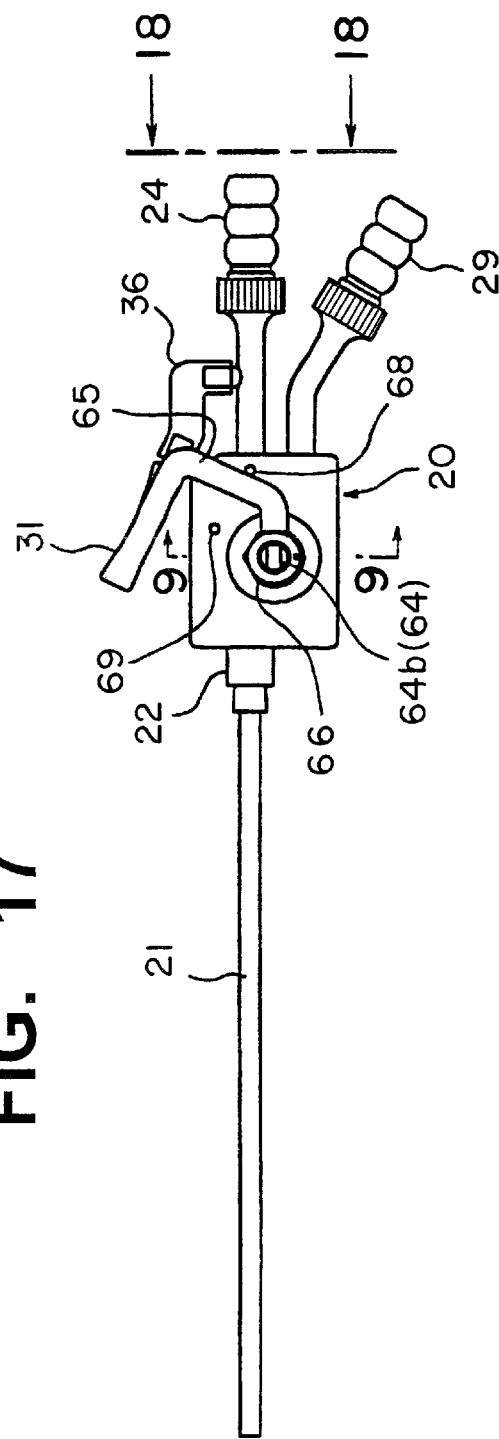

SUCTION DEVICE WITH IRRIGATION

BACKGROUND

This invention relates to a suction device with an irrigation function which can promptly switch from a treatment of sucking blood, neurolymph, pus, bone debris and the like from a surgical site to a treatment of irrigating to the site in a surgical operation, particularly nervi craniales operation.

In a nervi craniales operation, two different treatments, i.e., a treatment of sucking/removing blood and the like from a surgical site, and a treatment of irrigating/cleaning the site with an irrigation such as a physiological saline, are often alternately repeated. A suction device with an irrigation function provided with a valve capable of switching suction and irrigation is used to switch these treatments.

During a nervi craniales operation a surgeon is generally seeing into a microscope, while having a device such as a knife with one hand and the above suction device with the other hand. The operation often takes ten hours or more and the surgeon may become extremely tired. Thus, it is desirable that the surgeon can promptly and securely switch from a suction treatment to an irrigation treatment and vice versa only with the feeling of his hand without visual confirmation.

FIG. 27 is a sectional view showing a conventional suction device with an irrigation function as disclosed in Japanese Utility Model Kokai HEI2(1990)-86560. In this figure the reference numeral 1 denotes a probe body. The probe body 1 comprises: a generally cylindrical valve housing 2; three packing rings 3, 4 and 5 slidably accommodated in the valve housing 2; a groove part 6 formed between the packing rings 3 and 4; a groove part 7 formed between the packing rings 4 and 5; a valve 8 for pressing the upper part of the packing ring 3 toward the bottom part of the valve housing 2; a coil spring 9 disposed between the packing ring 5 and the bottom part of the valve housing 2 for urging upwardly the packing rings 3, 4 and 5; a suction tube 10 formed in the side wall of the valve housing 2; an irrigation tube 11 disposed under the suction tube 10; and a probe connection 13 disposed between the irrigation tube 11 and the suction tube 10 and connected to the proximal end of the probe 12 with the distal end of the probe 12 extending toward a surgical site.

Next, the action of the device will be explained. First, when carrying out a suction treatment, the valve 8 is not pressed against the packing ring 3 and the like. The packing ring 5 is urged upwardly by the coil spring 9 to obstruct or block the communication between the irrigation tube 11 and the probe 12, while the suction tube 10 communicates with the probe 12 through the groove part 7. As a result blood and the like can be sucked from a surgical site.

Next, when carrying out an irrigation treatment, the valve 8 is pressed against the packing ring 3 and the like to a maximum to block the communication between the suction tube 10 and the probe 12 by the packing ring 4. Since the irrigation tube 11 communicates with the probe 12 through the groove part 7, a psychological saline and the like can be supplied to the surgical site.

Japanese Utility Mode Kokai SH063(1988)-62109 also discloses a suction device in the substantially same construction as the conventional suction device as shown in FIG. 27.

However, in the suction device as shown in FIG. 27 the probe connection 13 with the probe 12 attached thereto communicates with the suction tube 10 in a crank-like form, not straightly, in the valve housing 2. Thus, wastes such as bone debris sucked from a surgical site may hit the side wall of the valve housing 2 between the suction tube 10 and the irrigation tube 11 to accumulate in the valve housing 2. Ultimately it may cause jamming in the valve housing 2, the suction tube 10 and the like thereby requiring the device to be replaced during a significant surgical operation. Further when the valve 8 is pressed to and kept at a position between the position for carrying out the suction treatment (suction position) and the position for carrying out the irrigation treatment (irrigation position), the packing ring 4 and the packing ring 5 cannot sufficiently block the suction tube 10 and the irrigation tube 11, respectively. Consequently, both the suction tube 10 and the irrigation tube 11 simultaneously communicate with the probe 12. Since a sucking force decreases, wastes such as bone debris sucked from a surgical site tend to hit on the side wall of the valve housing 2 between the suction tube 10 and the irrigation tube 11 and the periphery of the groove part 7, thereby dropping and accumulating in the valve housing 2. In this state, if a user presses the valve 8 to a maximum, a physiological saline for irrigation may be mixed with the above wastes. The saline containing the wastes can be supplied to a surgical site as a cleaning liquid to contaminate the surgical site.

SUMMARY OF THE INVENTION

The invention has been made to solve the above subject. An object of the invention is to provide a suction device with an irrigation function with the occurrence of jamming extremely reduced and which can be easily manipulated.

According to an aspect of the invention, there is provided a suction device with an irrigation function comprising; a suction device body, suction and irrigation tubes connected to the suction device body, a flexible tube having proximal and distal ends, the proximal end connected to the suction device body, and the distal end extending toward a surgical site, and a switch mechanism in the suction device body for switching communication between the flexible tube and the suction tube, and communication between the flexible tube and the irrigation tube; and characterized in that the suction tube is substantially straightly aligned with the flexible tube through inside of the suction device body.

According to another aspect of the invention, the device is characterized in that the switch mechanism comprises a valve body disposed at an intersection of the irrigation tube and a line connecting between the flexible tube and the suction tube, and a rotation lever for controlling opening and closing of the valve body.

According to another aspect of the invention, the device is characterized in that the valve body comprises a first valve body for switching communication and non-communication between the flexible tube and the suction tube inside the suction device body and a second valve body for switching communication and non-communication between the flexible tube and the irrigation tube inside the suction device body.

According to another aspect of the invention, the device is characterized in that the first valve body is a rotation valve body which is rotated in association with a rotation of the rotation lever to switch the communication and non-communication between the flexible tube and the suction tube; the second valve body is a projection member which is pressed by the rotation lever or released to switch the communication and non-communication between the flexible tube and the irrigation tube; and when the rotation lever contacts the second valve body, the flexible tube does not communicate with any one of the suction tube and the irrigation tube.

According to another aspect of the invention, the device is characterized in that a suction pressure fine control hole communicating with the suction tube and the atmosphere is provided in the rotation lever.

Accordingly to another aspect of the invention, the device is characterized in that the suction tube, the irrigation tube or the flexible tube is removably connected to the suction device body.

BRIEF DESCRIPTION OF THE DRAWINGS

FIG. 5 is sectional views of FIG. 2 along the line V—V, (a) shows an irrigation control mechanism in a suction state, (b) shows the irrigation control mechanism in a zero point state, and (c) shows the irrigation control mechanism in an irrigation state.

FIG. 10 is a plan view showing a suction device with an irrigation function according to the embodiment 2 of the invention.

FIG. 12 is a side view of FIG. 10.

FIG. 16 is a plan view showing a suction device with an irrigation function according to the embodiment 3 of the invention.

FIG. 17 is a side view of FIG. 16.

DETAILED DESCRIPTION OF THE INVENTION

Figure 1:
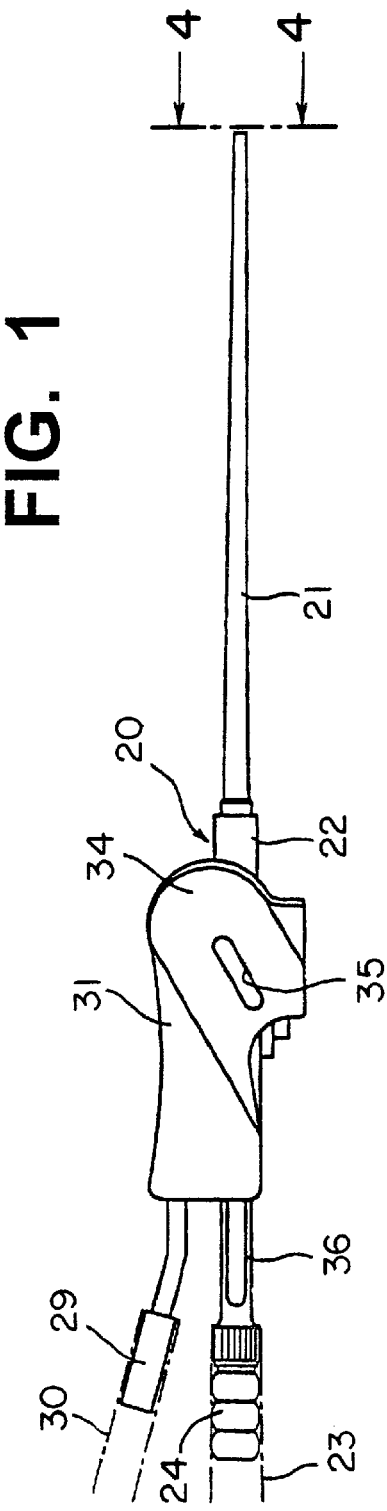
FIG. 1 is a plan view showing a suction device with an irrigation function according to the embodiment 1 of the invention.

Now, embodiments of the invention will be explained.

Embodiment 1

FIGS. 1 to 7 illustrate a first embodiment of a suction device according to the present invention. In these figures, unless indicated, the front of a device body is the side which a flexible tube with the distal end extending toward a surgical site is connected to, and the rear thereof is the side which is apart from the flexible tube.

In these figures, the reference numeral 20 denotes a suction device body of a generally box-like form. A flexible tube connection 22 is formed at the front of the suction device body 20, and a suction tube connection 24 is formed at the rear thereof. The proximal end of a flexible tube 21 with the distal end extending toward a surgical site is removably coupled to the flexible tube connection 22. The distal end of a suction tube 23 is removably coupled to the suction tube connection 24. The flexible tube 21 is substantially straightly aligned with the suction tube 23 through the inside of the suction device body 20. The "substantially straight alignment" used herein means that both the tubes are aligned on the same axis through the inner space of the suction device body 20, or that both the tubes are not aligned on the same axis but an end surface of the suction tube 23 with a larger diameter faces an end surface of the flexible tube 21 with a smaller diameter. However, when both the tubes are not aligned on the same axis but an end surface of the suction tube 23 with a smaller diameter faces an end surface (proximal end) of the flexible tube 21 with a larger diameter bone debris and the like sucked from a surgical site through a tip (distal end) of the flexible tube 21 cannot smoothly flow through the suction tube 23 and therefore the object of the invention is not disadvantageously accomplished. A drum-like rotation valve body (first valve body) 26 for opening or closing a suction path 25 is interposed in the suction path 25 to straightly connect between the flexible tube connection 22 and the suction tube connection 24. A irrigation path 27 is branched from the suction path 25 in advance of the rotation valve body 26. A piston-like projection member (second valve body) 28 is interposed in the irrigation path 27 for opening or closing the irrigation path 27. The irrigation path 27 is connected to an irrigation tube 30 through an irrigation tube connection 29 formed near the rear of the suction device body 20.

A shaft receiving part (not shown) is formed in the upper rear part of the suction device body 20. A rotation lever 31 is rotatably mounted in the shaft receiving part (not shown) through a shaft 32. The reference numeral 33 denotes an E-ring for securing the shaft 32 in the shaft receiving part (not shown). A torsion spring (not shown) is wound about the shaft 32, which spring normally urges the rotation lever 31 in a direction of standing up the lever 31. As shown in FIG. 1, a concave part 34 ergonomically designed to receive a finger operating the rotation lever 31 is formed in the upper part of the rotation lever 31. An elongated hole 35 for fine control of a suction pressure is provided at the center of the concave part 34. This suction pressure fine control hole 35 allows the communication between the suction path 25 and atmosphere through a branched path (not shown) inside the rotation lever 31 and a flexible tube 36.

A pending part 37 is formed at a side of the rotation lever 31. The pending part 37 has an elongated slide hole 38 extending along the length of the rotation lever 31 in its under part.

Figure 2:
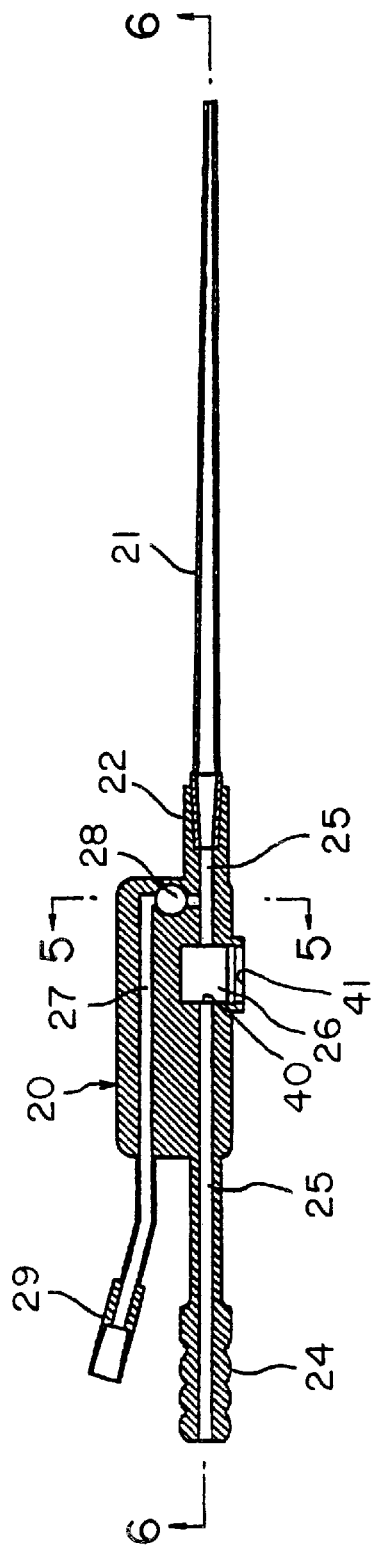
FIG. 2 is a sectional view of FIG. 1.
Figure 3:
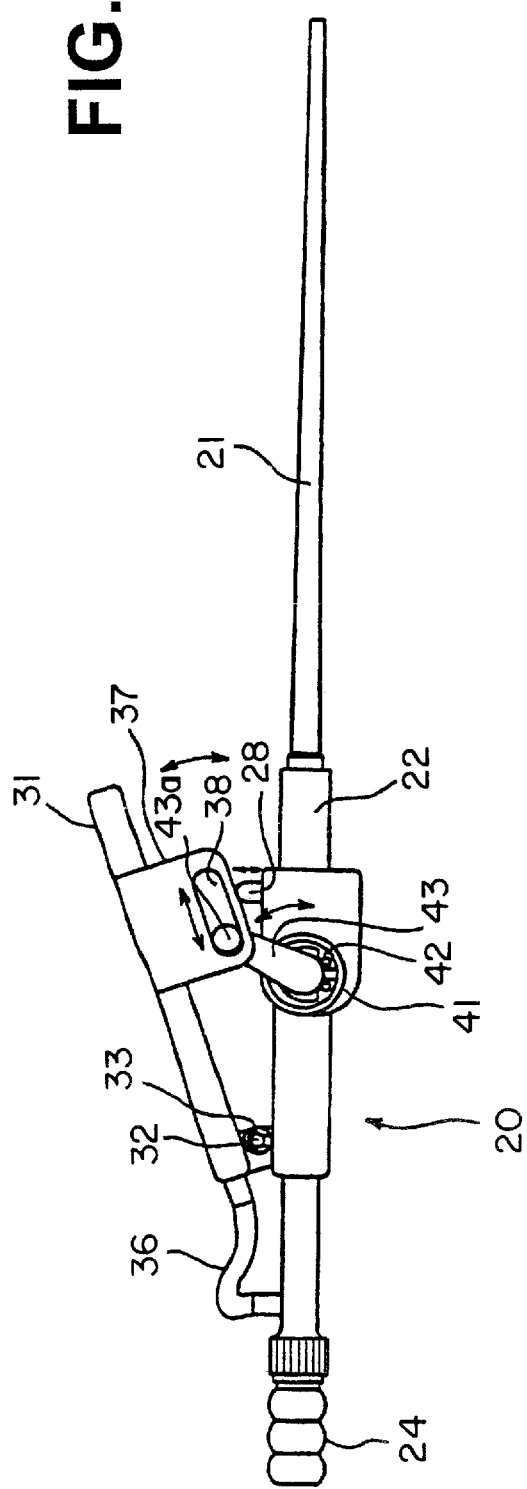
FIG. 3 is a side view of FIG. 1.
Figure 4:
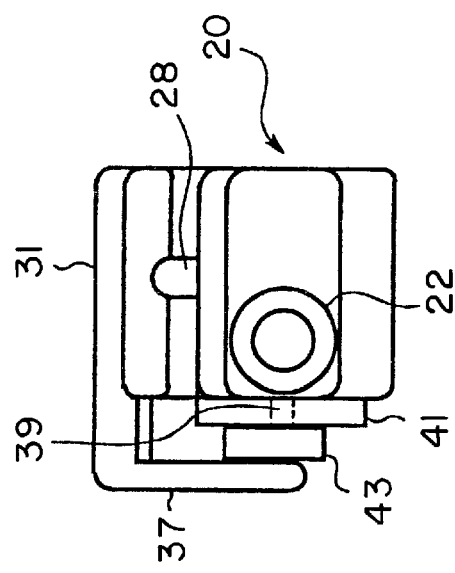
FIG. 4 is a view of FIG. 1 looking from the direction shown by the arrows IV.

As shown in FIGS. 2 and 4, the rotation valve body 26 is disposed in a cylindrical holding chamber 40 formed in the suction device body 20 so that the rotation valve body 26 can rotate about a rotation shaft 39 extending in the direction perpendicular to the suction path 25. A communication part 26a is formed inside the rotation valve body 26 and extends in the direction of the diameter. The holding chamber 40 has an opening 41 at a side of the suction device body 20. A C-ring 42 is mounted in the opening 41 to avoid the outward projection of the rotation valve body 26. One end of the rotation shaft 39 is fixed to the rotation valve body 26, and the other end thereof is fixed to an end (not shown) of a crank lever 43 through the opening 41. The other end 43a of the crank lever 43 is slidably mounted in the slide hole 38 of the rotation lever 31.

As shown in FIGS. 5(a) to 5(c), the projection member 28 of an elongated piston-like shape comprises a top part 28a exposed outside from a hole 44 of the suction device body 20, and a communication part 28b disposed under the top part 28a and constituting a part of the irrigation path 27. A coil spring 45 is placed between the projection member 28 and the bottom part of the above hole 44 to normally upwardly urge the projection member 28. In addition, a plurality of O-rings 46a, 46b and 46c are placed in the inner wall of the hole 44 of the suction device body 20 and the outer wall of the projection member 28 for sealing against air or liquid.

Next the action of the device will be explained.

Figure 6A:
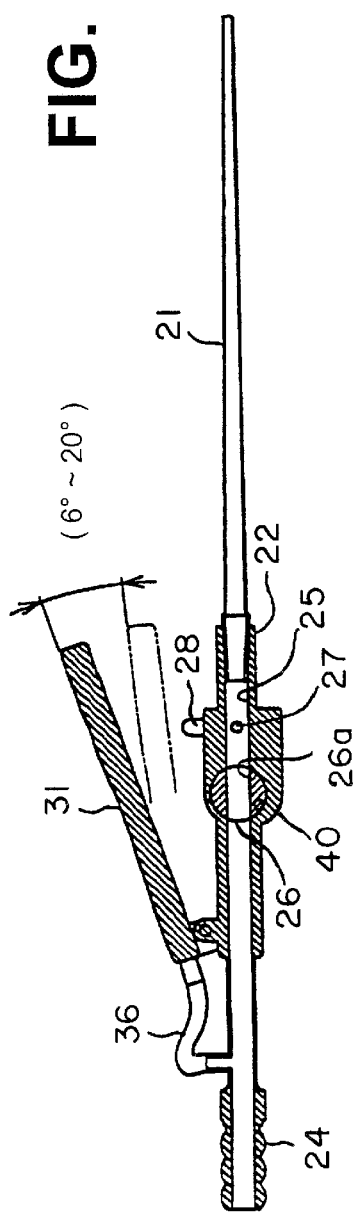
FIG. 6 is sectional views of FIG. 2 along the line VI—VI, (a) shows a suction control mechanism in a suction state, (b) shows the suction control mechanism in a zero point state, and (c) shows the suction control mechanism in an irrigation state.

First, for transferring to the suction state, the rotation lever 31 is not pressed. As shown in FIG. 6(a), when the rotation lever 31 is urged by the torsion spring (not shown) to stand to a maximum, the suction path 25 can communicate with the flexible tube 21 through the communication part 26a of the rotation valve body 26 secured to the rotation lever 31 through the crank lever 43, thereby becoming in the suction state. On the other hand, as shown in FIG. 5(a), since the top part 28a of the projection member 28 is not downwardly pressed by the rotation lever 31, the projection member 28 is lifted to the highest position by the urging force of the coil spring 45 to separate the suction path 25 from the irrigation path 27 by the under part of the communication part 28b of the projection member 28. In the embodiment 1, a rotation angle of the rotation lever 31 (hereinafter referred to as lever angle) ranges from 20 degrees to −3 degrees against the horizontal plane, but the invention is not limited to this range.

Next, as the rotation lever 31 is gradually declined at lever angles of 6 degrees to 20 degrees, the rotation valve body 26 is correspondingly gradually rotated. Accordingly, the open area of the communication part 26a of the rotation valve body 26 against the suction path 25 decreases with gradual decreases in suction pressure. In the situation where the suction pressure fine control hole 35 of the rotation lever 31 is completely opened, as the rotation lever 31 is rotated, the suction pressure linearly decreases along the line L1 in FIG. 7. In the situation where the suction pressure fine control hole 35, is completely closed, as the rotation lever 31 is rotated, the suction pressure linearly decreases along the line L2 in FIG. 7. That is, the suction pressure may change within the range of the region Z in FIG. 7 by using the suction pressure fine control hole 35.

Figure 6B:
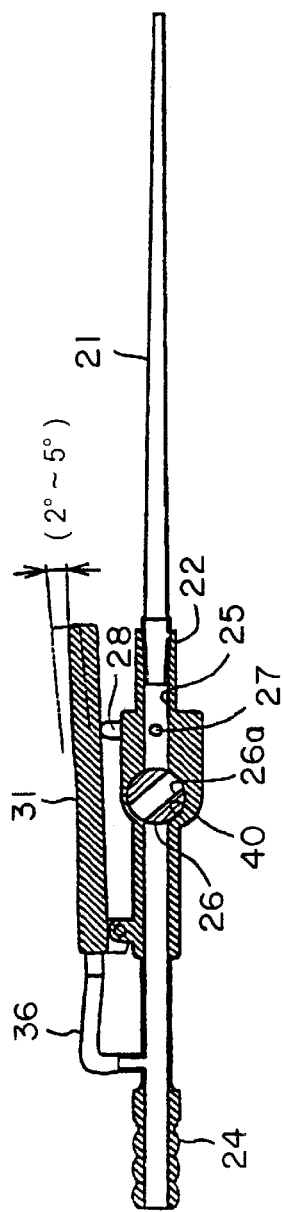
Figure 6C:
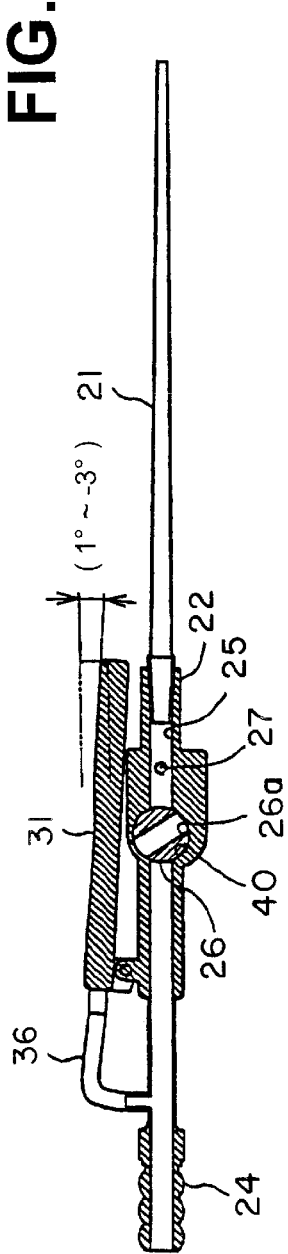
Figure 7:
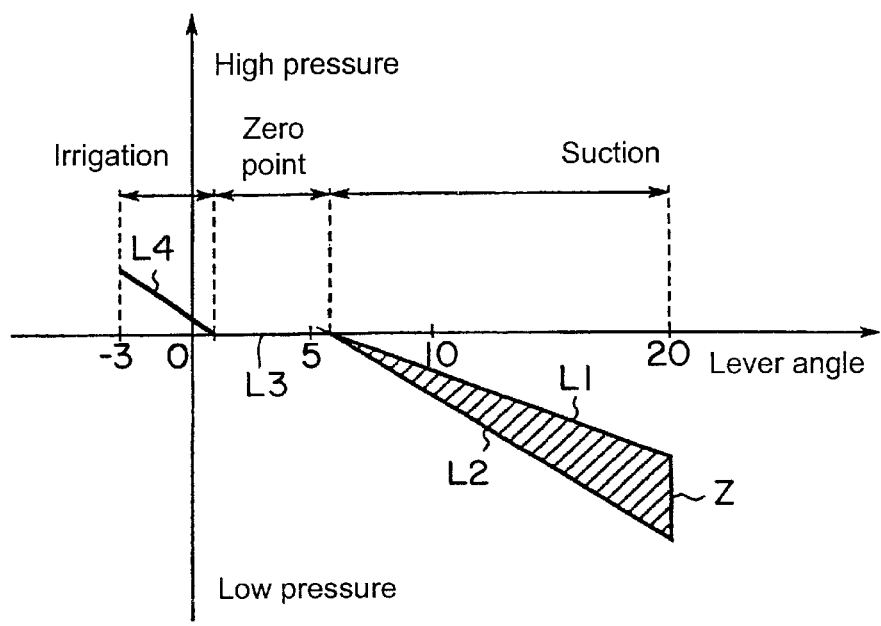
FIG. 7 is a graph showing the relationship between lever angles and pressures of a rotation lever controlling both the suction and irrigation control mechanisms.

Next, as the rotation lever 31 is declined at lever angles of 2 degrees to 5 degrees, the under surface of the rotation lever 31 comes in contact with the top part 28a of the projection member 28 to generate a contact sound as shown in FIGS. 5(b) and 6(b). The communication part 26a of the rotation valve body 26 is completely disconnected from the suction path 25, and any materials are not sucked through the flexible tube 21. Further, the communication part 28b of the projection part 28 does not allow the communication between the irrigation path 27 and the suction path 25. Thus, this state which is neither the "suction state" nor the "irrigation state" is called as zero point state" meaning a neutral state. A surgeon can confirm the "zero point state" by oscillation and contact sound generated when the rotation lever 31 comes in contact with the projection member 28, without looking at the device held by his hand. In this state, the suction pressure does not change as indicated by the line L3 in FIG. 7.

Next, as the rotation lever 31 is further declined at lever angles of 1 degree to −3 degrees, the top part 28a of the projection member 28 is pressed by the under surface of the rotation lever 31 to lower the projection member 28, overcoming the urging force of the coil spring 45, while the suction path 25 is closed by the rotation valve body 26 as mentioned above, as shown in FIGS. 5(c) and 6(c). The open area of the communication part 28b of the projection member 28 against the suction path 25 and irrigation path 27 gradually increases. Such an "irrigation state" is shown by the line L4 in FIG. 7. When the rotation lever 31 is released the "irrigation state" returns to the "suction state" through the "zero point state" by the urging force of the torsion spring (not shown).

As mentioned above, according to the embodiment 1, the suction path 25 is straightly aligned with the flexible tube 21 through the inside of the suction device body 20. Thus, in the suction state, bone debris and the like sucked from a surgical site through the tip of the flexible tube 21 can smoothly flow without jamming in the suction device body 20 and the like, reducing the replacement frequency of the device during a surgical operation.

Further, according to the embodiment 1, the rotation lever 31 is used to set the "zero point state" in addition to the "suction state" and the "irrigation state". Thus, a surgeon can have time to select either returning to the "suction state" or transferring to the "irrigation state", in the state that neither "suction" nor "irrigation" is carried out. That is, the device can be manipulated with ease and accuracy.

Further, according to the embodiment 1, the opening and closing of the rotation valve body 26 (first valve body) is associated with those of the projection member 28 (second valve body) such that both the valve bodies are not simultaneously opened. Thus, both "suction" and "irrigation" do not simultaneously proceed without contaminating a surgical site, unlike the conventional suction device. As a result, a surgical operation can be safely conducted.

Figure 27:
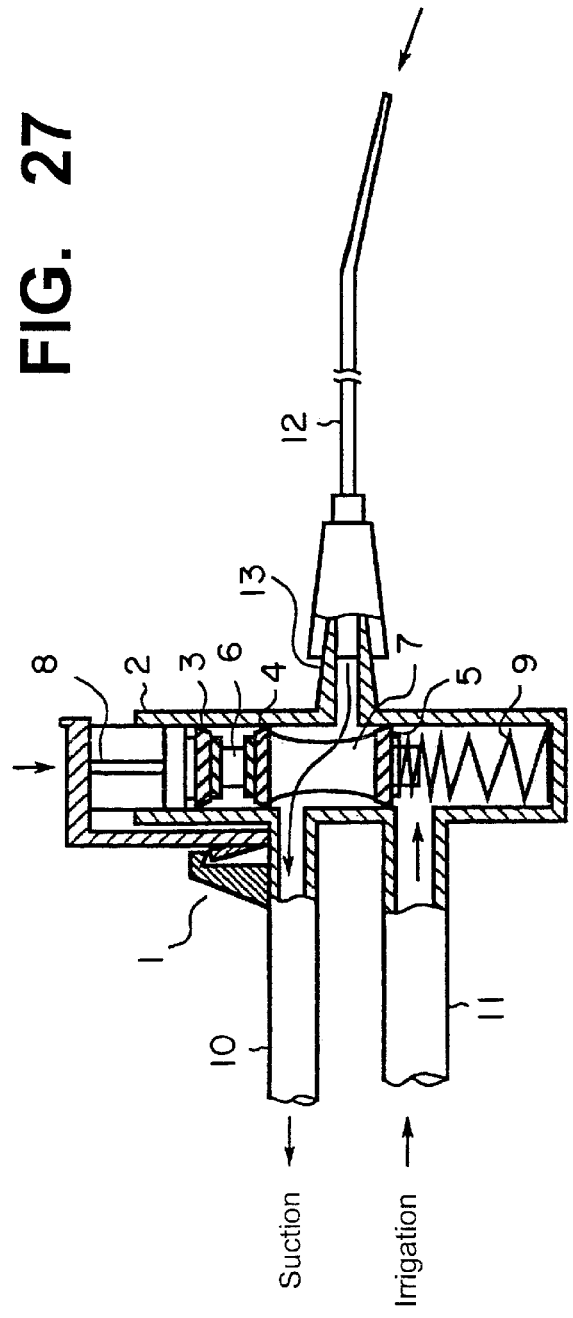
FIG. 27 is a sectional view showing a prior art suction device with an irrigation function.

Further, according to the embodiment 1, the opening degrees of the rotation valve body 26 (first valve body) and the projection member 28 (second valve body) are controlled by a rotation of the rotation lever 31. In the conventional suction device as shown in FIG. 27, the opening degree of the valve body is controlled by the reciprocation of the piston. Since the stroke of the rotation lever 31 necessary for the control is longer than that of the piston, a reduced pressure in the suction state or the flow amount of a physiological saline and the like in the irrigation state can be accurately controlled.

Further, according to the embodiment 1, the suction pressure fine control hole 35 is provided in the rotation lever 31. Thus, in addition to the first adjustment of a suction pressure by a rotation of the rotation lever 31 the second adjustment thereof can be effected by the suction pressure fine control hole 35. There can be provided a suction device suitable for nervi craniales operations requiring the extremely delicate adjustment of a suction pressure.

Further, although the suction pressure fine control hole 35 is provided in the rotation lever 31 in the embodiment 1, the hole 35 may be omitted when a surgeon can finely control a suction pressure only by the rotation lever 31.

Figure 8:
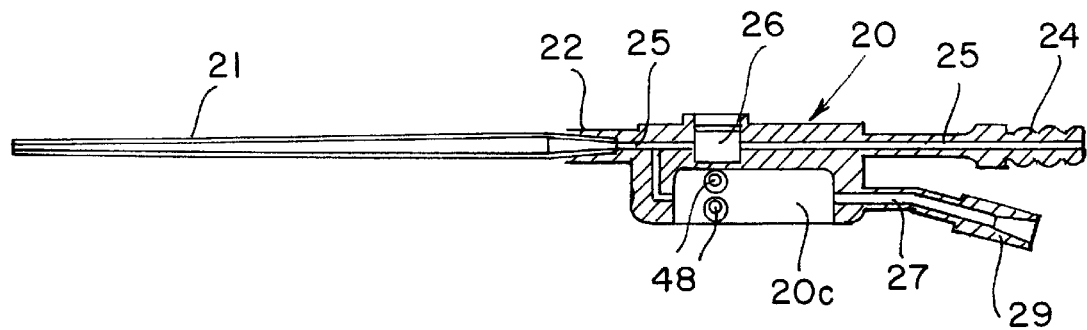
FIG. 8 is a sectional view showing a modification of the suction device with an irrigation function according to the embodiment 1 of the invention.
Figure 9:
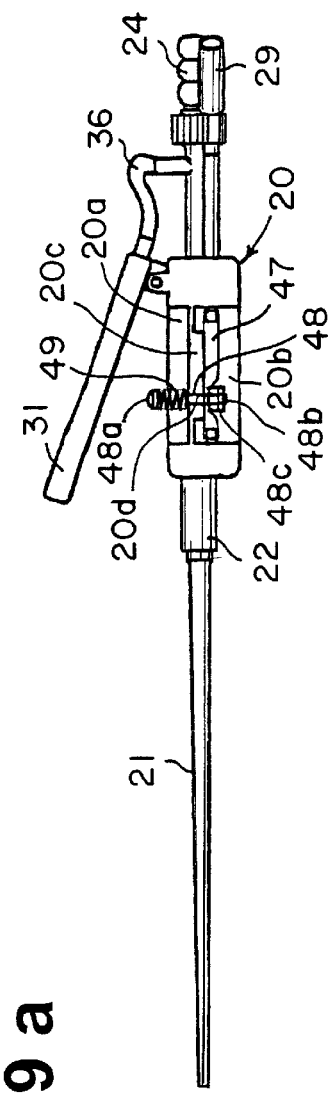
FIG. 9 is side view of FIG. 8, (a) shows an irrigation control mechanism in a suction state, (b) shows the irrigation control mechanism in a zero point state, and (c) shows the irrigation control mechanism in an irrigation state.
Figure 9:
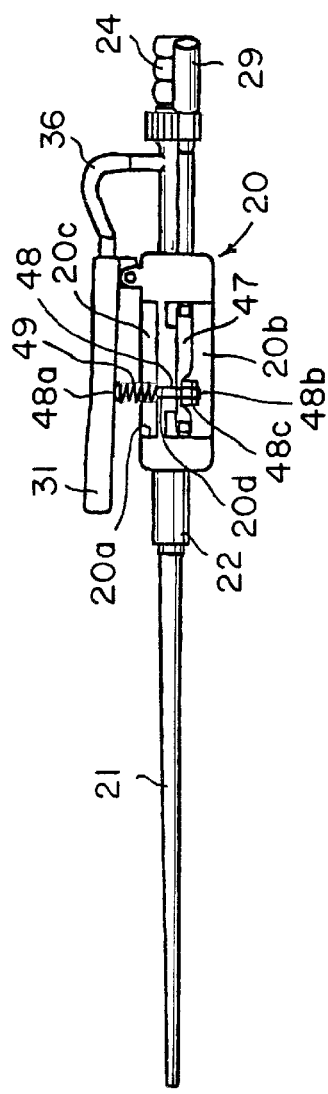
Figure 9:
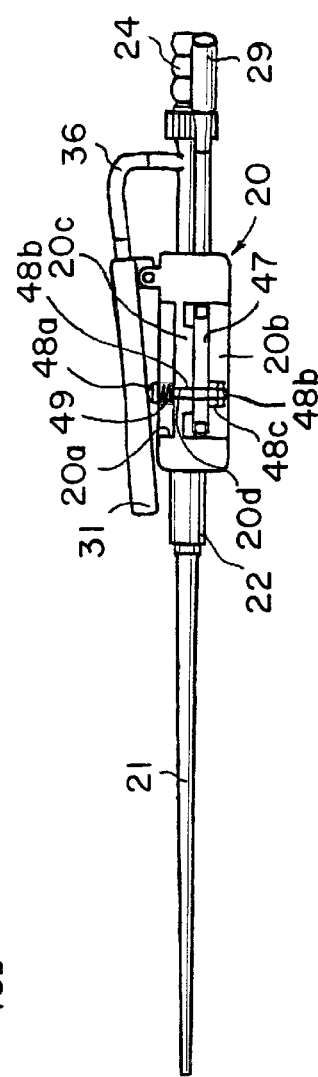
Figure 11:
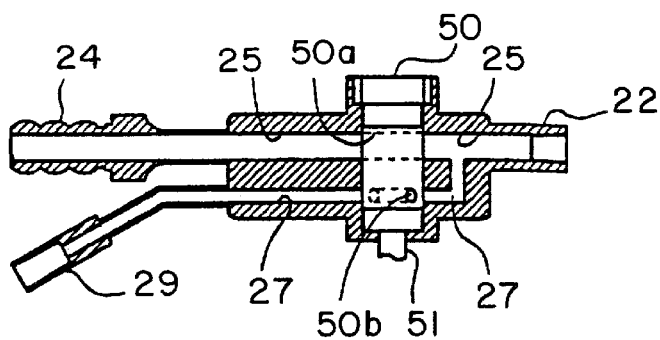
FIG. 11 is a sectional view of FIG. 10.
Figure 13:
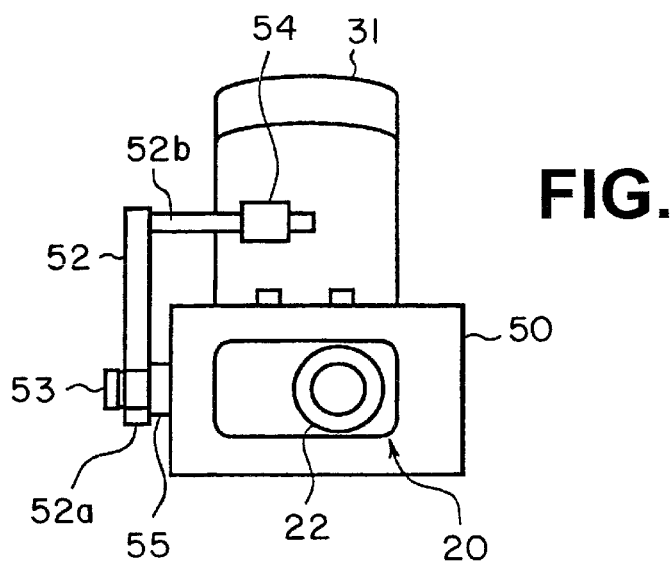
FIG. 13 is a view of FIG. 12 looking from the direction shown by the arrows XIII.

Although the projection member 28 opens or closes the rigid irrigation path 27 in the embodiment 1, a part of the irrigation path 27 can be replaced with a flexible tube 47 as shown in FIGS. 8 and 9. In this case, the irrigation path 27 inside the suction device body 20 is cut out by a certain distance and the flexible tube 47 is interposed and connected between end parts of the cut irrigation paths 27. Upper and under concave parts 20a and 20b are formed between the end parts of the out irrigation paths 27 in the upper and under sides of the suction device body 20, respectively, and a support plate 20c is provided between the concave parts 20a and 20b. A pair of holes 20d are aligned in the support plate 20c in the direction perpendicular to the length of the flexible tube 47. The two projection members 48 of the same shape are mounted in the pair of holes 20d, respectively. Coil springs 49 are wound between the top parts 48a of the projection members 48 and the support plate 20c. Legs 48b of both the projection members 48 are integrated by a coupling member 48c. The flexible tube 47 Is sandwiched between the legs 48b of the projection members 48 as well as between the coupling member 48c and the support plate 20c.

In the "suction state", as shown in FIG. 9(a), since the top parts 48a of the projection members 48 are not downwardly pressed by the rotation lever 31, the projection members 48 are lifted against the support plate 20c by the urging forces of the coil springs 49. As a result, the flexible tube 47 sandwiched between the support plate 20c and the coupling member 48c is collapsed to close the irrigation path 27. In the "zero point state", as shown in FIG. 9(b), since the top parts 48a of the projection members 48 are slightly downwardly pressed by the rotation lever 31 but the projection members 48 is hardly lowered, the flexible tube 47 remains collapsed between the support plate 20c and the coupling member 48c. In the "irrigation state", as shown in FIG. 9(c), since the top parts 48a of the projection members 58 are further downwardly pressed by the rotation lever 31, the projection members 48 are lowered to generate a space between the support plate 20c and the coupling member 48c. As a result, the flexible tube 47 is not collapsed to open the irrigation path 27 through the flexible tube 47.

Suitable flexible tubes 47 include a silicon tube. When the flexibility of the flexible tube 47 decreases, it can be easily replaced with a new flexible tube.

Embodiment 2

FIGS. 10 to 15 illustrate a second embodiment of a suction device according to the present invention. In the embodiment 2, like reference numerals denote like components of the embodiment 1, and overlapping explanation thereof is omitted.

A feature of the embodiment 2 is that one drum-like rotation valve body 50 formed by integrating a first valve body for suction control and a second valve body for irrigation control is provided so as to straddle a suction path 25 and an irrigation path 27. Another feature thereof is that as a rotation lever 31 is rotated, the rotation valve body 50 is rotated so that a communication part 50a or 50b of the rotation valve body 20 can separately communicate the suction path 25 or the irrigation path 27 at different timings. These features will be described in detail below.

As mentioned above, the rotation valve body 50 is located so as to straddle the suction path 25 and the irrigation path 27. The communication part 50a is formed in the position corresponding to the suction path 25 along the diameter of the rotation valve body 50, while the communication part 50b is formed in the position corresponding to the irrigation path 27 at a certain angle with respect to the communication part 50a along the diameter of the rotation valve body 50. That is, when the communication part 50a is in the horizontal position or the suction path 25 communicates with the flexible tube 21, the communication part 50b is placed at an angle α with respect to the horizontal plane. This angle α corresponds to a rotation angle of a second rotation lever as described later.

A rotation shaft 51 is attached to an end of the rotation valve body 50. A generally L-shaped rotation lever 52 comprises a part 52a of which an end 52a is fixed to the rotation shaft 51 by an E-ring 53, and a part 52b which is bent so as to be parallel to the rotation shaft 51. A roller 54 is rotatably attached to an end of the rotation lever 52. The rotation lever 52 is normally urged by a torsion spring 55 wound about the rotation shaft 51 in the direction of standing up the lever 52. The roller 54 is normally in contact with the under surface of the first rotation lever 31 by this urging force. Thus, as the rotation lever 31 is rotated, the roller 54 runs on the under surface, of the rotation lever 31 and the rotation lever 52 is also rotated at the same time.

Next, the action of the device will be explained.

Figure 14A:
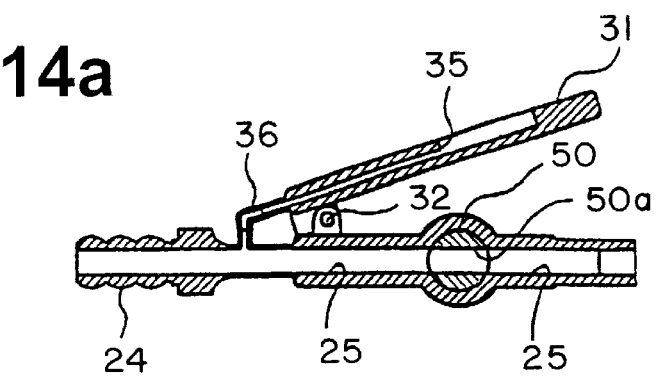
FIG. 14 is sectional views of FIG. 10 along the line XIV—XIV, (a) shows a suction control mechanism in a suction state, and (b) shows the suction control mechanism in an irrigation state.
Figure 15A:
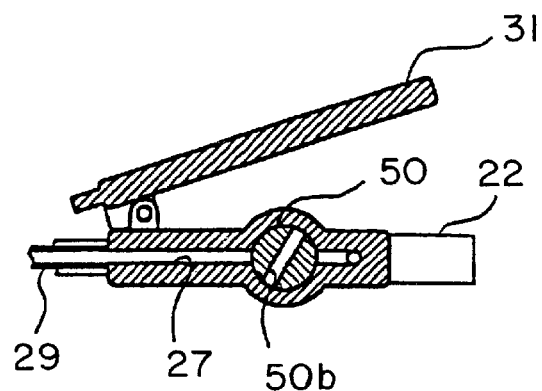
FIG. 15 is sectional views of FIG. 10 along the line XV—XV, (a) shows an irrigation control mechanism in a suction state, and (b) shows the irrigation control mechanism in an irrigation state.
Figure 15B:
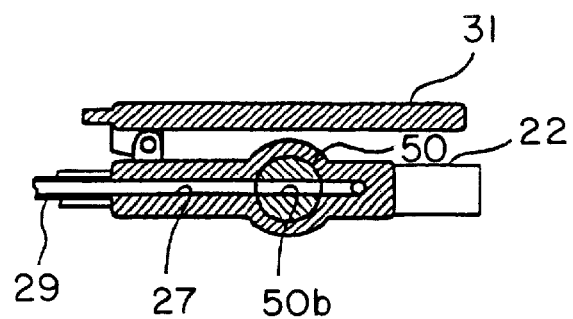
Figure 18:
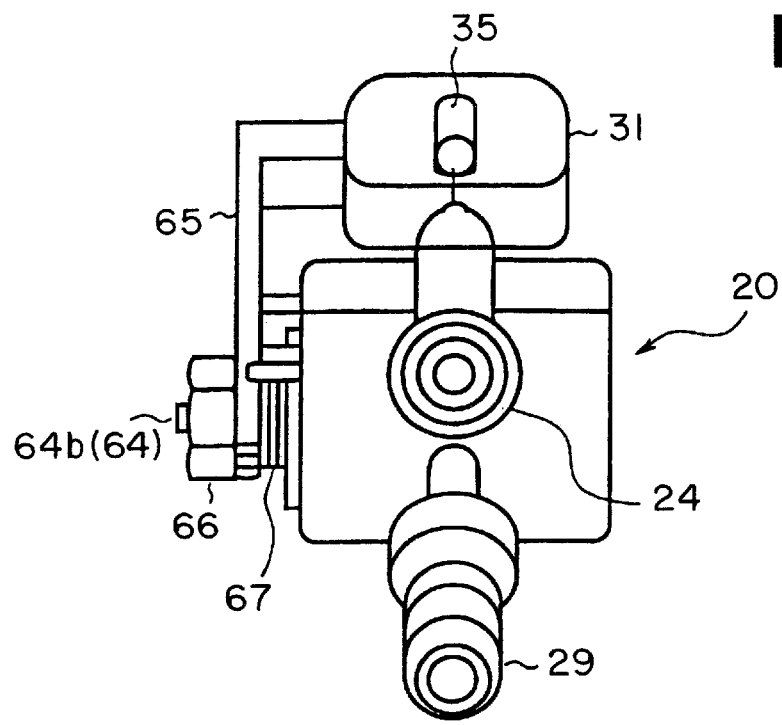
FIG. 18 is a view of FIG. 17 looking from the direction shown by the arrows XVIII.

For transferring to the suction state, the rotation lever 31 is not pressed. When the rotation lever 31 stands up to a maximum by the urging force of the torsion spring (not shown), the rotation lever 52 correspondingly also stands up to a maximum. At this time, as shown in FIG. 14(a), the suction path 25 communicates with the flexible tube 21 through the communication part 50a of the rotation valve body 50, thereby transferring to the suction state. However, as shown in FIG. 15(a), since the communication part 50b is inclined at the angle α with respect to the irrigation path 27, an irrigation tube connection 29 does not communicate with the flexible tube 21.

Then, as the rotation lever 31 is gradually declined, the rotation valve body 50 is gradually rotated. Accordingly, the open area of the communication part 50a of the rotation valve body 50 against the suction path 25 decreases with gradual decreases in suction pressure. In this suction state, a suction pressure fine control hole 35 formed in the rotation lever 31 can be used to finely control a suction pressure. In other words, if both the rotation lever 31 and the suction pressure fine control hole 35 are used, a suction pressure can be controlled at two stages.

Further, when the rotation lever 31 is declined so that the open area of the communication part 50*a* of the rotation valve body 50 against the suction path 25 reaches to zero, the open area of the other communication part 50*b* against the irrigation path 27 also remains zero. This state is the "zero point state" where neither "suction" nor "irrigation" is carried out. A method of confirming the transformation to the "zero point state" is not essential for the invention. For example, a pawl to be bounced by the rotation lever 52 may be provided in a certain position of the outer wall of the suction device body 20. A sound generated when the rotation lever 52 bounces the pawl can be used for confirmation of the "zero point state".

Figure 14B:
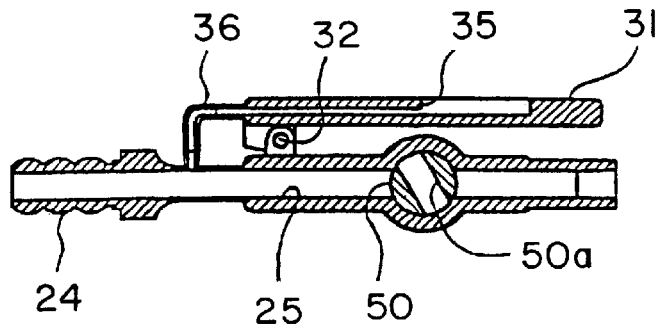

Next, as the rotation lever 31 is further declined, as shown in FIGS. 14(*b*) and 15(*b*), the open area of the communication part 50*b* of the rotation valve body 50 against the irrigation path 27 gradually increases, while the suction path 25 is closed by the rotation valve body 50 as mentioned above. Finally, the irrigation bath 27 communicates with the flexible tube 21 through the communication part 50*b* of the rotation valve body 50 to become in the irrigation state.

As mentioned above, according to the embodiment 2, similarly to the embodiment 1, the suction path 25 is straightly aligned with the flexible tube 21 through the inside of the suction device body 20. Thus, in the suction state, bone debris and the like sucked from a surgical site through the tip of the flexible tube 21 can smoothly flow without jamming in the suction device body 20 and the like, reducing the replacement frequency of the device during a surgical operation.

Further, according to the embodiment 2, the rotation lever 31 is used to set the "zero point state" in addition to the "suction state" and the "irrigation state". Thus, a surgeon can have time to select either returning to the "suction state" or transferring to the "irrigation state", in the state that neither "suction" nor "irrigation" is carried out. That is, the device can be manipulated with ease and accuracy.

Further, according to the embodiment 2, the two communication parts 50*a* and 50*b* of the rotation valve body 50 do not simultaneously communicate with the suction path 25 and the irrigation path 27. Thus, both "suction" and "irrigation" do not simultaneously proceed without contaminating a surgical site, unlike the conventional suction device. As a result, a surgical operation can be safely conducted.

Further, according to the embodiment 2, the open areas of the two communication parts 50*a* and 50*b* of the rotation valve body 50 against the suction path 25 and the irrigation path 27 are controlled by a rotation of the rotation lever 31. In the conventional suction device as shown in FIG. 27, the opening degree of the valve body is controlled by the reciprocation of the piston. Since the stroke of the rotation lever 31 necessary for the control is longer than that of the piston, a reduced pressure in the suction state or the flow amount of a physiological saline and the like in the irrigation state can be accurately controlled.

Further, according to the embodiment 2, the two communication parts 50*a* and 50*b* are provided in the one rotation valve body 50. Thus, if these communication parts 50*a* and 50*b* become jammed, only the rotation valve body 50 can be cleaned or replaced, thereby facilitating maintenance.

Further, according to the embodiment 2, the suction pressure fine control hole 35 is provided in the rotation lever 31. Thus, in addition to the first adjustment of a suction pressure by a rotation of the rotation lever 31, the second adjustment thereof can be effected by the suction pressure fine control hole 35. There can be provided a suction device suitable for nervi craniales operations requiring the extremely delicate adjustment of a suction pressure.

Embodiment 3

FIGS. 16 to 21 show a third embodiment of a suction device according to the present invention. In the embodiment 3, like reference numerals denote like components of the embodiment 1, and overlapping explanation thereof is omitted.

A feature of the embodiment 3 is that a ball-like rotation valve body 60 is used instead of the drum-like rotation valve body of the embodiment 2. The feature will be explained in detail below.

Figure 19:
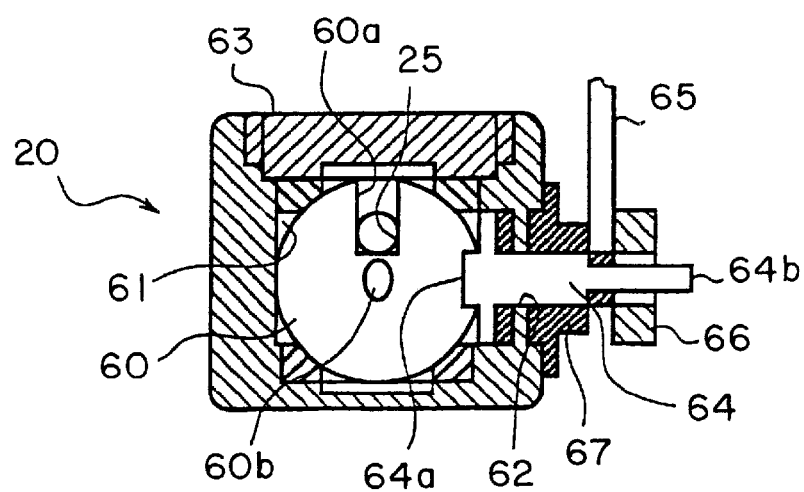
FIG. 19 is a sectional view of FIG. 17 along the line XIX—XIX.
Figure 20:
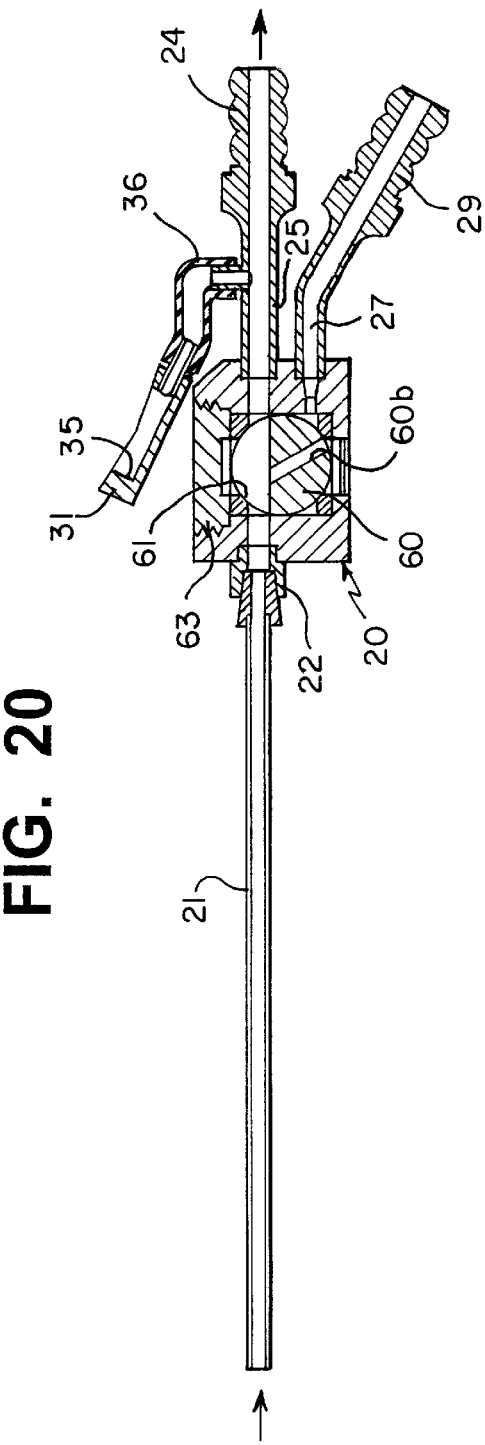
FIG. 20 is a sectional view of FIG. 16 along the line XX—XX showing a suction state.
Figure 21:
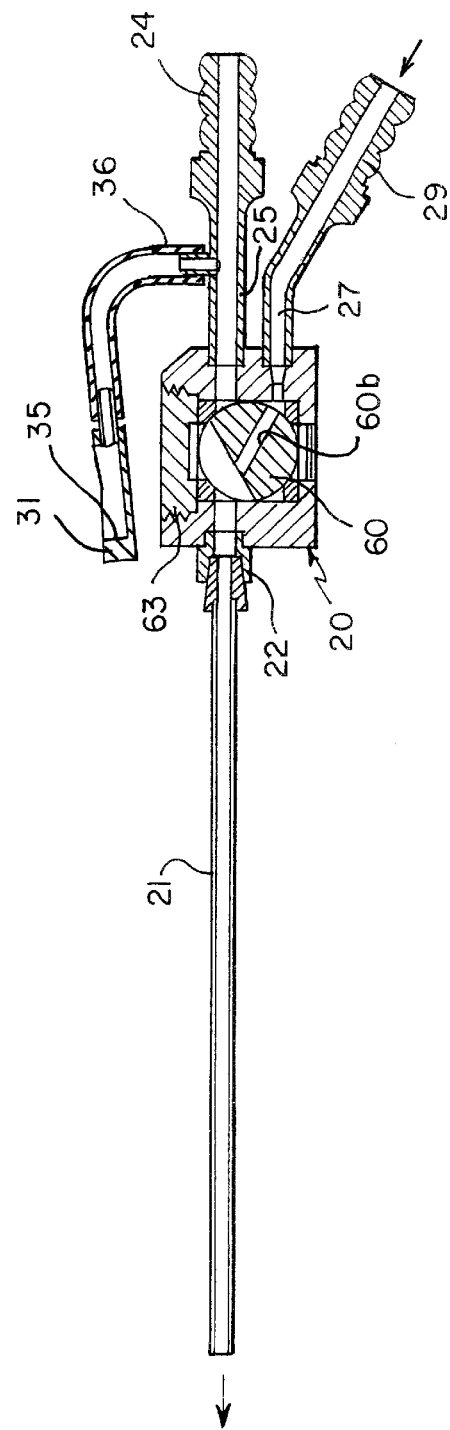
FIG. 21 is a sectional view of FIG. 16 along the line XXI—XXI showing an irrigation state.
Figure 22:
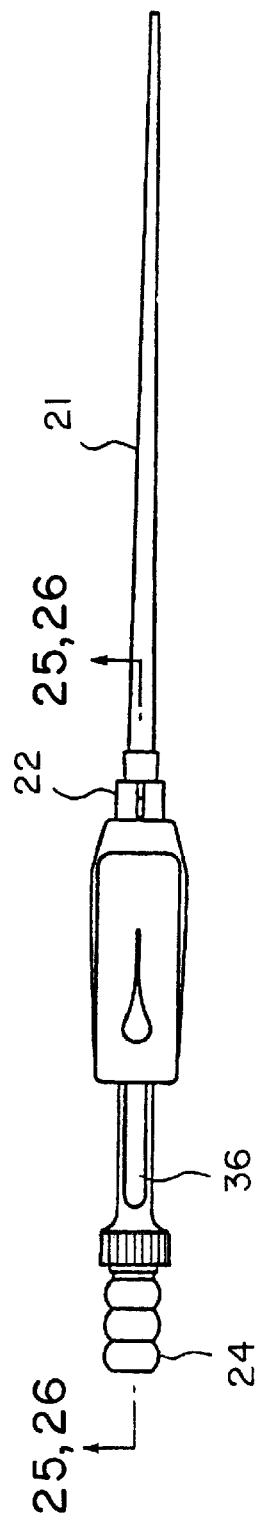
FIG. 22 is a plan view showing a suction device with an irrigation function according to the embodiment 4 of the invention.
Figure 23:
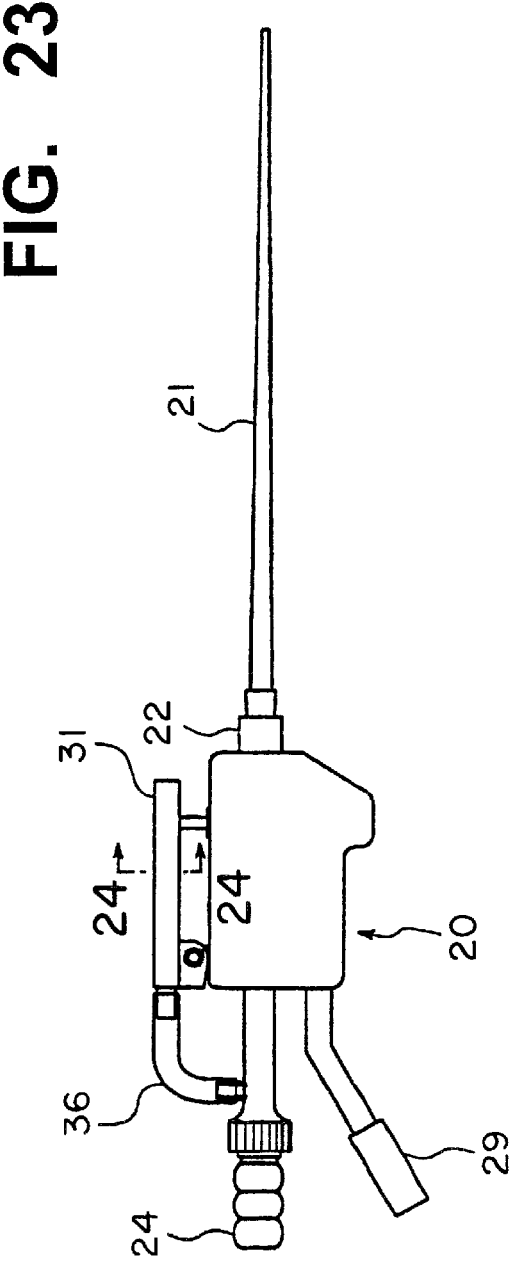
FIG. 23 is a side view of FIG. 22.

As shown in FIGS. 19 to 21, a rotation valve body 60 comprising a first communication part 60*a* and a second cylindrical communication part 60*b* is accommodated in a holding chamber 61 in a suction device body 20. The first communication part 60*a* is a groove containing a chord and a corresponding arc, and the cylindrical communication part 60*b* is inclined from the first communication part 60*a* at a certain angle. A flexible tube connection 22, a suction path 25 substantially straightly aligned with the connection 22 and an irrigation path 27 disposed under the suction path 25 are connected to the holding chamber 61. As shown in FIG. 19, an opening 62 is formed at a side of the holding chamber 61 and a lid 63 is mounted in the upper part thereof.

An end 64*a* of a shaft 64 is fixed to the periphery of the rotation valve body 60 In the direction perpendicular to the lengths of the communication parts 60*a* and 60*b*. The other end 64*b* of the shaft 64 has a generally plate-like shape. A screw (not shown) is formed outside the shaft 64. When the rotation valve body 60 is held in the holding chamber 61, the end 64*b* is exposed outside from the opening 62. The end 64*b* is engaged with an opening (not shown) formed in an end of an arm 65 integrally formed at a side of a rotation lever 31 so that the rotation valve body 60 can be rotated in association with a rotation of the rotation lever 31. The reference numeral 66 denotes a nut for preventing the arm 65 from being disengaged from the shaft 64. Further, a torsion spring 67 is wound about the shaft 64, which spring 67 urges the arm 65 in the direction of standing up the rotation lever 31. Two pins 68, 69 are projected on the outer wall of the suction device body 20 for limiting the rotation angle of the arm 65.

Next, the action of the device will be explained.

First, for transferring to the suction state, the rotation lever 31 is not pressed. As shown in FIGS. 19 and 20, when the rotation lever 31 stands up to a maximum by the urging force of the torsion spring 67, the suction path 25 communicates with the flexible tube 21 through the communication part 60*a* of the rotation valve body 60, thereby transferring to the suction state. However, since the communication part 60*b* does not communicate with the irrigation path 27 an irrigation tube connection 29 does not communicate with the flexible tube 21.

Then, as the rotation lever 31 is gradually declined, the rotation valve body 60 is gradually rotated. Accordingly, the open area of the communication part 60*a* of the rotation valve body 60 against the suction path 25 decreases with gradual decreases in suction pressure. In this suction state, a suction pressure fine control hole 35 formed in the rotation lever 31 can be used to control a suction pressure at two stages.

Further, when the rotation lever 31 is declined so that the open area of the communication part 60*a* of the rotation valve body 60 against the suction path 25 reaches to zero, the open area of the other communication part 60*b* against the irrigation path 27 also remains zero. This state is the "zero point state" where neither suction nor "irrigation" is carried out. A method of confirming the transformation to the "zero point state" is not essential for the invention. For example, a pawl to be bounced by the arm 65 may be provided in a certain position of the outer wall of the suction device body 20. A sound generated when the arm 65 bounces the pawl can be used for confirmation of the "zero point state".

Next, as the rotation lever 31 is further declined, as shown in FIG. 21, the open area of the communication part 60*b* of the rotation valve body 60 against the irrigation path 27 gradually increases, while the suction path 25 is closed by the rotation valve body 60 as mentioned above. Finally, the irrigation path 27 communicates with the flexible tube 21 through the communication part 60*b* of the rotation valve body 60 to become in the irrigation state. When the rotation lever 31 is released, the "irrigation state" returns to the "suction state" through the "zero point state" by the urging force of the torsion spring (not shown).

As mentioned above, according to the embodiment 3, similarly to the embodiments 1 and 2, the suction path 25 is straightly aligned with the flexible tube 21 through the inside of the suction device body 20. Thus, in the suction state, bone debris and the like sucked from a surgical site through the tip of the flexible tube 21 can smoothly flow without jamming in the suction device body 20 and the like, reducing the replacement frequency of the device during a surgical operation.

Further, according to the embodiment 3, the rotation lever 31 is used to set the "zero point state" in addition to the "suction state" and the "irrigation state". Thus, a surgeon can have time to select either returning to the "suction state" or transferring to the "irrigation state", in the state that neither "suction" nor "irrigation" is carried out. That is, the device can be manipulated with ease and accuracy.

Further, according to the embodiment 3, the two communication parts 60*a* and 60*b* of the rotation valve body 60 do not simultaneously communicate with the suction path 25 and the irrigation path 27. Thus, both "suction" and "irrigation" do not simultaneously proceed without contaminating a surgical site, unlike the conventional suction device. As a result, a surgical operation can be safely conducted.

Further, according to the embodiment 3, the open areas of the two communication parts 60*a* and 60*b* of the rotation valve body 60 against the suction path 25 and the irrigation path 27 are controlled by a rotation of the rotation lever 31. In the conventional suction device as shown in FIG. 27, the opening degree of the valve body is controlled by the reciprocation of the piston. Since the stroke of the rotation lever 31 necessary for the control is longer than that of the piston, a reduced pressure in the suction state or the flow amount of a physiological saline and the like in the irrigation state can be accurately controlled.

Further, according to the embodiment 3, the two communication parts 60*a* and 60*b* are provided in the one rotation valve body 60. Thus, if these communication parts 60*a* and 60*b* become jammed, only the rotation valve body 60 can be cleaned or replaced, thereby facilitating maintenance.

Further, according to the embodiment 3, the suction pressure fine control hole 35 is provided in the rotation lever 31. Thus, in addition to the first adjustment of a suction pressure by a rotation Of the rotation lever 31, the second adjustment thereof can be effected by the suction pressure fine control hole 35. There can be provided a suction device suitable for nervi craniales operations requiring the extremely delicate adjustment of a suction pressure.

Embodiment 4

FIGS. 22 to 26 show a fourth embodiment of a suction device according to the present invention. In the embodiment 4, like reference numerals denote like components of the embodiment 1, and overlapping explanation thereof is omitted.

A feature of the embodiment 4 is that a piston-like valve body 70 is coupled to a rotation lever 31, and opening and closing of the valve body 70 is associated with a rotation of the rotation lever 31. The feature will be explained in detail below.

Figure 24:
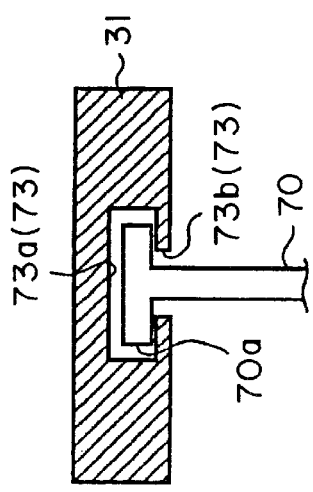
FIG. 24 is a sectional view of FIG. 23 along the line XXIV—XXIV.
Figure 25:
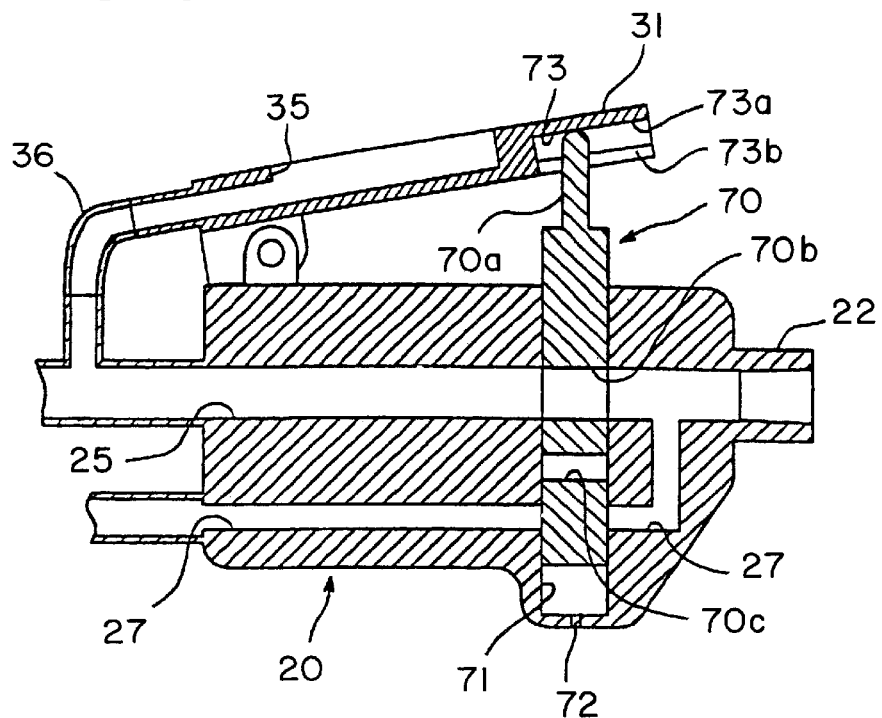
FIG. 25 is a sectional view of FIG. 22 along the line XXV—XXV showing a suction state.
Figure 26:
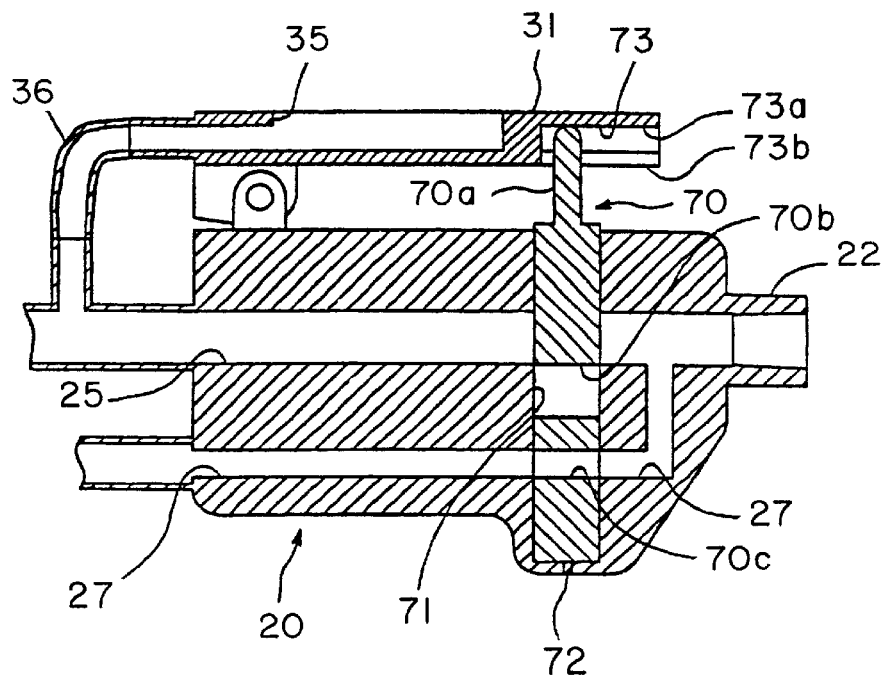
FIG. 26 is a sectional view of FIG. 22 along the line XXVI—XXVI showing an irrigation state.

The valve body 70 is accommodated in a hole 71 of a suction device body 20 so that the valve body 70 can move upwardly and downwardly. As shown in FIGS. 24 to 26, the valve body 70 comprises a generally T-shaped top part 70*a*, a first communication part 70*b* formed at the center of the valve body 70 in the horizontal direction, and a second communication part 70*c* formed under the first communication part 70*b*. A flexible tube connection 22, a suction path 25 substantially straightly aligned with the connection 22 and an irrigation path 27 disposed under the suction path 25 are connected to the hole 71 of the suction device body 20. Since the distance between the first communication part 70*b* and the second communication, part 70*c* is shorter than that between the suction path 25 and the irrigation path 27, both the communication parts 70*b* and 70*c* are not simultaneously connected to both the paths 25 and 27 when the valve body 70 moves upwardly or downwardly. A plurality of O-rings (not shown) are provided in the inner wall of the hole 71 of the suction device body 20 for sealing against air and liquid. A hole 72 opening to the atmosphere is formed in the bottom part of the hole 71 for the adjustment of the pressure inside the hole 71 and the disposal of bone debris and the like.

The top part 70*a* of the valve body 70 is accommodated in a slide groove 73 formed in the under part of an end of the rotation lever 31. An opening 73*a* is formed and sized such that the lateral part of the T-shaped top part 70*a* can pass through, while an opening 73*b* under the opening 73*a* is formed and sized such that only the longitudinal part thereof can pass through. Thus, the valve body 70 can move upwardly and downwardly following a rotation of the rotation lever 31.

Next, the action of the device will be explained.

First, for transferring to the suction state, the rotation lever 31 is not pressed. As shown in FIG. 25, when the rotation lever 31 stands up to a maximum by the urging force of the torsion spring (not shown), the valve body 70 is lifted and the suction path 25 communicates with the flexible tube 21 through the communication part 70*b* of the valve body 70, thereby transferring to the suction state. However, since the communication part 70*c* does not communicate with the irrigation path 27, an irrigation tube connection 29, does not communicate with the flexible tube 21.

Then, as the rotation lever 31 is gradually declined, the valve body 70 is gradually lowered. Accordingly, the open area of the communication part 70*b* of the valve body 70 against the suction path 25 decreases with gradual decreases in suction pressure. In this suction state, a suction pressure fine control hole 35 formed in the rotation lever 31 can be used to control a suction pressure at two stages.

Further, when the rotation lever 31 is declined so that the open area of the communication part 70*b* of the valve body 70 against the suction path 25 reaches to zero, the open area of the other communication part 70c against the irrigation path 27 also remains zero. This state is the "zero point state" where neither "suction" nor "irrigation" is carried out. A method of confirming the transformation to the "zero point state" is not essential for the invention.

Next, as the rotation lever 31 is further declined, as shown In FIG. 26 the open area of the communication part 70c of the valve body 70 against the irrigation path 27 gradually increases, while the suction path 25 is closed by the valve body 70 as mentioned above. Finally, the irrigation path 27 communicates with the flexible tube 21 through the communication part 70c of the valve body 70 to become in the irrigation state.

As mentioned above, according to the embodiment 4, similarly to the embodiments 1 to 3, the suction path 25 is straightly aligned with the flexible tube 21 through the inside of the suction device body 20. Thus, in the suction state, bone debris and the like sucked from a surgical site through the tip of the flexible tube 21 can smoothly flow without jamming in the suction device body 20 and the like, reducing the replacement frequency of the device during a surgical operation.

Further, according to the embodiment 4, the rotation lever 31 is used to set the "zero point state" in addition to the "suction state" and the "irrigation state". Thus, a surgeon can have time to select either returning to the "suction state" or transferring to the "irrigation state", in the state that neither "suction" nor "irrigation" is carried out. That is, the device can be manipulated with ease and accuracy.

Further, according to the embodiment 4, the two communication parts 70b and 70c of the valve body 70 do not simultaneously communicate with the suction path 25 and the irrigation path 27. Thus, both "suction" and "irrigation" do not simultaneously proceed without contaminating a surgical site, unlike the conventional suction device. As a result, a surgical operation can be safely conducted.

Further, according to the embodiment 4, the open areas of the two communication parts 70b and 70c of the valve body 70 against the suction path 25 and the irrigation path 27 are controlled by a rotation of the rotation lever 31. In the conventional suction device as shown in FIG. 27, the opening degree of the valve body is controlled by the reciprocation of the piston. Since the stroke of the rotation lever 31 necessary for the control is longer than that of the piston, a reduced pressure in the suction state or the flow amount of a physiological saline and the like in the irrigation state can be accurately controlled.

Further, according to the embodiment 4, the two communication parts 70b and 70e are provided in the one valve body 70. Thus, if these communication parts 70b and 70c become jammed, only the valve body 70 can be cleaned or replaced, thereby facilitating maintenance.

Further, according to the embodiment 4, the suction pressure fine control hole 35 is provided in the rotation lever 31. Thus, in addition to the first adjustment of a suction pressure by a rotation of the rotation lever 31, the second adjustment thereof can be effected by the suction pressure fine control hole 35. There can be provided a suction device suitable for nervi craniales operations requiring the extremely delicate adjustment of a suction pressure.

As mentioned above, according to the invention, the suction path is straightly aligned with the flexible tube through the inside of the suction device body. Thus, in the suction state, bone debris and the like sucked from a surgical site through the tip of the flexible tube can smoothly flow without jamming in the suction device body and the like, reducing the replacement frequency of the device during a surgical operation.

Further, according to the invention, the rotation lever is used to set the "zero point state" in addition to the "suction state" and the "irrigation state". Thus, a surgeon can have time to select either returning to the "suction state" or transferring to the "irrigation state", in the state that neither "suction nor "irrigation" is carried out. That is the device can be manipulated with ease and accuracy. Further, according to the invention, the two communication parts of the valve body do not simultaneously communicate with the suction path and the irrigation path. Thus, both "suction" and "irrigation" do not simultaneously proceed without contaminating a surgical site, unlike the conventional suction device. As a result, a surgical operation can be safely conducted.

Further, according to the invention, the open areas of the two communication parts of the valve body against the suction path and the irrigation path are controlled by a rotation of the rotation lever. In the conventional suction device, the opening degree of the valve body is controlled by the reciprocation of the piston. Since the stroke of the rotation lever necessary for the control is longer than that of the piston, a reduced pressure in the suction state or the flow amount of a physiological saline and the like in the irrigation state can be accurately controlled.

Further, according to the invention, the two communication parts are provided in the one valve body. Thus, if these communication parts become jammed, only the valve body can be cleaned or replaced, thereby facilitating maintenance.

Further, according to the invention, the suction pressure fine control hole is provided in the rotation lever. Thus, in addition to the first adjustment of a suction pressure by a rotation of the rotation lever, the second adjustment thereof can be effected by the suction pressure fine control hole. There can be provided a suction device suitable for nervi craniales operations requiring the extremely delicate adjustment of a suction pressure.

While the invention has been particularly described in connection with specific embodiments thereof, it is to be understood that this is by way of illustration and not of limitation, and that the scope of the appended claims should be construed as broadly as the prior art will permit.

What is claimed is:

1. A suction device with an irrigation function, comprising;

a suction device body, suction and irrigation tubes connected to the suction device body, a flexible tube having proximal and distal ends, the proximal end connected to the suction device body, and the distal end extending toward a surgical site, and a switch mechanism in the suction device body for switching communication between the flexible tube and the suction tube, and communication between the flexible tube and the irrigation tube;

the suction device being characterized in that the suction tube is substantially straightly aligned with the flexible tube through inside of the suction device body.

2. The suction device with an irrigation function of claim 1 characterized in that the switch mechanism comprises a valve body disposed at an intersection of the irrigation tube and a line connecting between the flexible tube and the suction tube, and a rotation lever for controlling opening and closing of the valve body.

3. The suction device with an irrigation function of claim 2 characterized in that the valve body comprises a first valve body for switching communication and non-communication between the flexible tube and the suction tube inside the suction device body, and a second valve body for switching communication and non-communication between the flexible tube and the irrigation tube inside the suction device body.

4. The suction device with an irrigation function of claim 3 characterized in that the first valve body is a rotation valve body which is rotated in association with a rotation of the rotation lever to switch the communication and non-communication between the flexible tube and the suction tube; the second valve body is a projection member which is pressed by the rotation lever or released to switch the communication and non-communication between the flexible tube and the irrigation tube; and when the rotation lever contacts the second valve body, the flexible tube does not communicate with any one of the suction tube and the irrigation tube.

5. The suction device with an irrigation function of claim 4 characterized in that a suction pressure fine control hole communicating with the suction tube and atmosphere is provided in the rotation lever.

6. The suction device with an irrigation function of any one of claims 1 to 5 characterized in that the suction tube, the irrigation tube or the flexible tube is removably connected to the suction device body.

7. A suction device with an irrigation function, comprising:

a suction device body, a suction tube and an irrigation tube connected to the suction device body, a flexible tube having a proximal end and a distal end, the proximal end connected to the suction device body, and the distal end extending toward a surgical site, and a valve in the suction device body for switching communication between the flexible tube and the suction tube, and communication between the flexible tube and the irrigation tube, the valve comprising a first valve body for switching communication and non-communication between the flexible tube and the suction tube inside the suction device body, the first valve body is a rotation valve body which is rotated to switch the communication and non-communication between the flexible tube and the suction tube, and a second valve body for switching communication and non-communication between the flexible tube and the irrigation tube inside the suction device body, the second valve body is a projection member which is pressed or released to switch the communication and non-communication between the flexible tube and the irrigation tube;

the suction tube is substantially straightly aligned with the flexible tube through inside of the suction device body.

8. The suction device with an irrigation function of claim 7, wherein the first valve body and the second valve body are disposed at an intersection of the irrigation tube and a line connecting between the flexible tube and the suction tube, and further comprising a rotation lever for controlling opening and closing of the first valve body and the second valve body.

9. The suction device with an irrigation function of claim 8, wherein when the rotation lever contacts the second valve body, the flexible tube does not communicate with any one of the suction tube and the irrigation tube.

10. The suction device with an irrigation function of claim 8, further comprising a suction pressure fine control hole disposed in the rotation lever, the suction pressure hose control hole communicating with the suction tube and atmosphere.

11. The suction device with an irrigation function of claim 7, wherein at least one of the suction tube, the irrigation tube and the flexible tube is removably connected to the suction device body.

* * * * *